(12) United States Patent
Asad et al.

(10) Patent No.: US 8,358,215 B2
(45) Date of Patent: Jan. 22, 2013

(54) ATTENTION ASSISTANCE AND MONITORING

(75) Inventors: Mohammad Asad, Dhaka (BD); Nathalia Peixoto, Ashburn, VA (US); Sidney West, Jr., Fairfax Station, VA (US); David Grossman, Vienna, VA (US)

(73) Assignee: George Mason Intellectual Properties, Inc., Fairfax, VA (US)

(*) Notice: Subject to any disclaimer, the term of this patent is extended or adjusted under 35 U.S.C. 154(b) by 98 days.

(21) Appl. No.: 13/093,407

(22) Filed: Apr. 25, 2011

(65) Prior Publication Data

US 2012/0098764 A1 Apr. 26, 2012

Related U.S. Application Data

(63) Continuation-in-part of application No. 12/785,733, filed on May 24, 2010.

(60) Provisional application No. 61/242,141, filed on Sep. 14, 2009.

(51) Int. Cl.
*G08B 23/00* (2006.01)

(52) U.S. Cl. ..................................... 340/573.1; 340/575

(58) Field of Classification Search ............... 340/573.1, 340/575
See application file for complete search history.

(56) References Cited

U.S. PATENT DOCUMENTS

| 6,147,612 A | * | 11/2000 | Ruan et al. | 340/575 |
| 2011/0012742 A1 | * | 1/2011 | Johnson | 340/669 |
| 2011/0169635 A1 | * | 7/2011 | Johnson | 340/540 |

* cited by examiner

*Primary Examiner* — Travis Hunnings
(74) *Attorney, Agent, or Firm* — David Grossman

(57) ABSTRACT

An attention assistance device configured to help maintain a user's focus on a given task. In one embodiment, text is presenting to a user on a touchscreen. The user tracking the text using a finger is monitored. The user is stimulated when the finger stops tracking the text for a predetermined period of time. In another embodiment, an electronic device presents an output configured to be tracked by a user. A monitoring device observes the user tracking the output. A sensory stimulating device stimulates the user when the "tracking" falls below an attention threshold.

23 Claims, 17 Drawing Sheets

ATTENTION ASSISTANCE AND MONITORING

CROSS-REFERENCE TO RELATED APPLICATIONS

This is a continuation-in-part application of U.S. application Ser. No. 12/785,733, filed May 24, 2010, which claims the benefit of U.S. Provisional Application No. 61/242,141, filed Sep. 14, 2009, which are hereby incorporated by reference in their entirety.

DETAILED DESCRIPTION OF EMBODIMENTS

Embodiments of the present invention relate to an attention assistance device and method of using such a device including various features that help maintain a user's focus on a given task.

Figure 1:
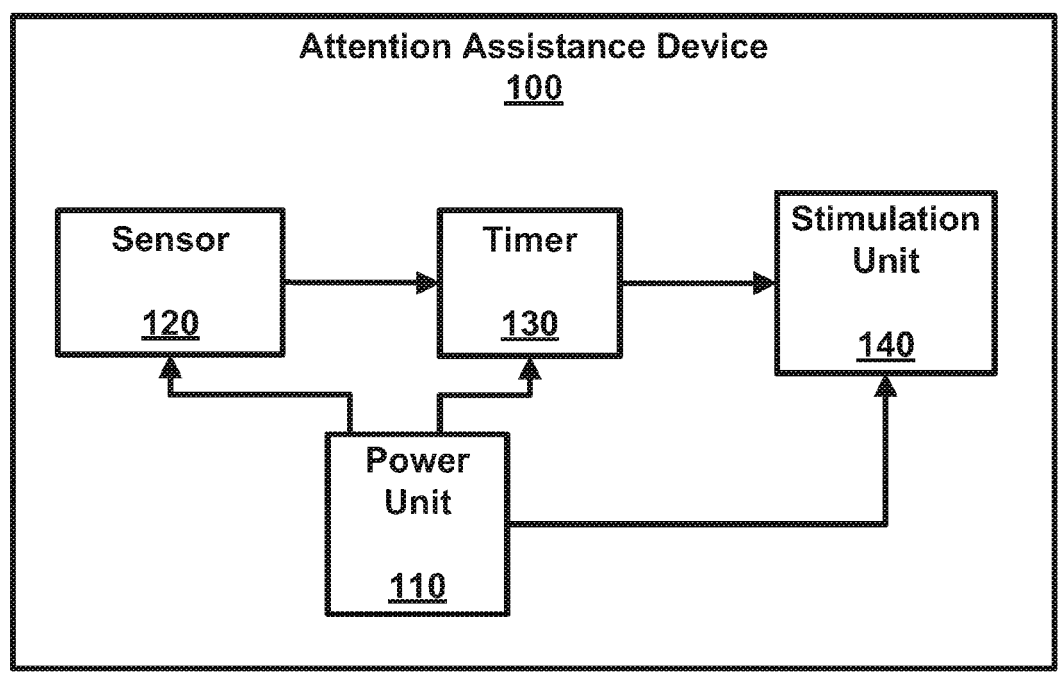
FIG. 1 is a block diagram showing an arrangement of an attention assistance device, as per an aspect of an embodiment of the present invention.

FIG. 1 shows a first arrangement of the attention assistance device 100 according to the present invention. The attention assistance device 100 may comprise a power unit 110 as a source for providing power to the various components of the device. The device 100 may also include a sensor 120, a timer 130, and a stimulation unit 140.

Examples of the power unit 110 include, but are not limited to, a battery (e.g., NiCad, L$^+$ ion, rechargeable, etc.), power control (which may have an automatic on/off/sleep selection component), etc. The power unit 110 may be used to generate power to all of the various components of the device including the stimulation unit 140.

The sensor 120 may be any kind of sensor (i.e., motion sensor, visual sensor, heat sensor, etc.) that detects a user's movement or use of the device 100. Nonlimiting examples of sensor 120 include a switch, a ball sensor, an optical emitter detector, an accelerometer, a rocking ball switch, a pressure sensor, and equivalents thereof.

The stimulation unit 140 may be any kind of stimulator capable of alerting the user. Nonlimiting examples of the stimulation unit 140 include a light or illumination source (which may be still, pulsating, strobe, blinking randomly or in a particular pattern, etc.), a vibrator, a sound emitter, a tactile object, a moving component (such as bimetal arms), an electric shock stimulator, wheels, etc.

Figure 2:
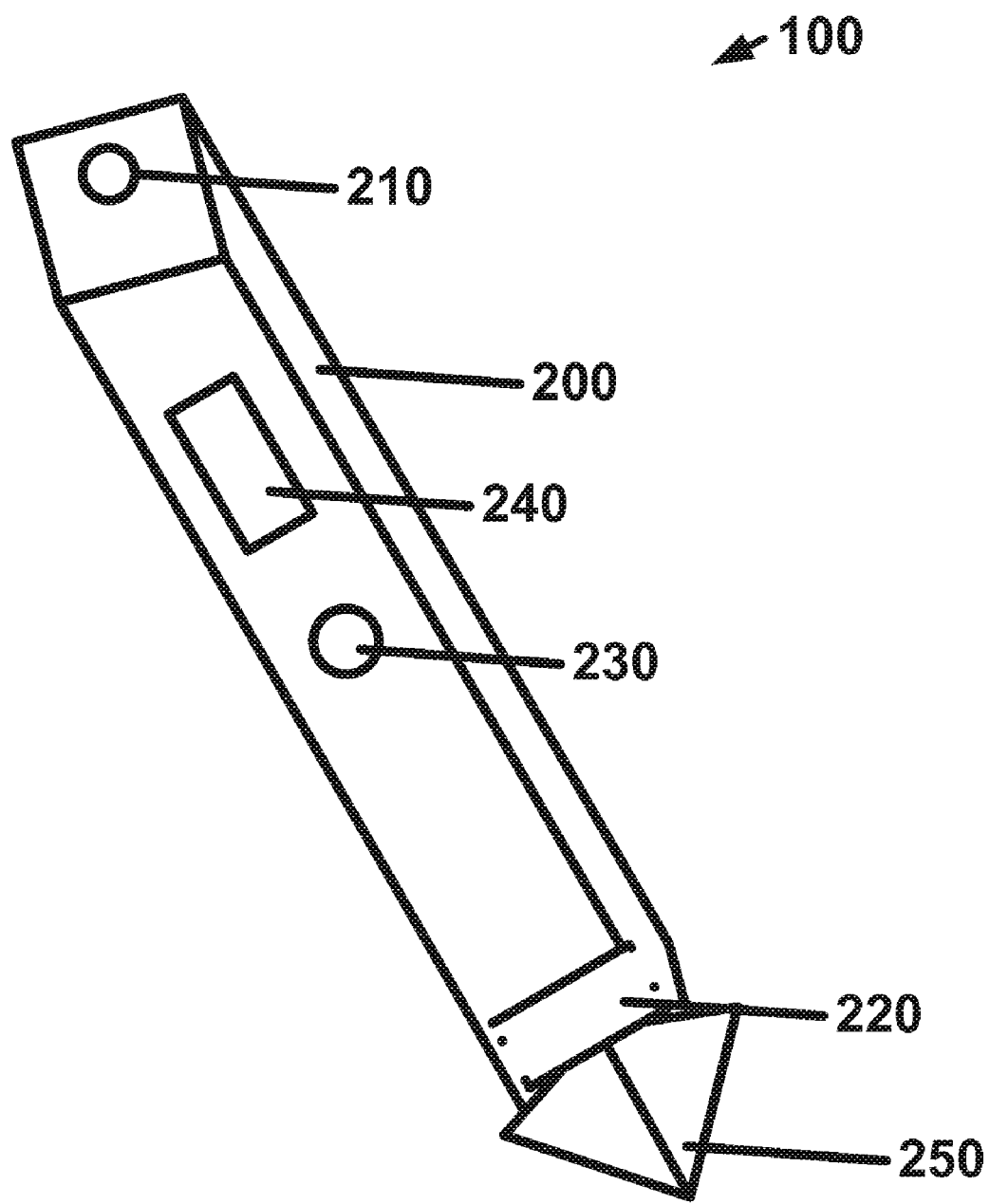
FIG. 2 is a perspective front view of an attention assistance device, as per an aspect of an embodiment of the present invention.

FIG. 2 illustrates a three-dimensional view of one arrangement of the attention assistance device 100. The device 100 may have a case 200 that may be in the shape of a writing instrument or pointer. On the case 200, there may be a display window 240 for displaying a variety of information to the user. The information displayed may include one or more of, for example, the number of detected inattention episodes, performance of stimulators, the time it took to regain attention (sensor redetecting attention assistance device usage) after being stimulated, activity sensor output history, stimulation unit activation frequency, timer history, battery life, date, time, progress meter, and type of stimulation used. A button or switch 230 (or other user interface such as a dial, a knob, a touchscreen display, etc.) may also be arranged on the case 200 to power the device on and off, and for the user to provide an input to the device 100. At one end of the case 200, the light or illumination source 210 as a stimulator unit may be positioned to alert the user or indicate to the user that the device 100 is in a particular state.

In alternative arrangements, the case may be a tube resembling a pen, mechanical pencil, pencil, pointer, watch, wristband, part of a flash drive device, highlighter, bookmark, cell phone, personal data assistant (PDA), mobile telecommunications device, electronic tablet etc. The device 100 may also be housed as one component of a combination of the casings listed above to create a combinatorial device (e.g., a device with a highlighter and/or one or more pens attached).

One way to detect whether the device 200 is in use or not is that the sensor 220 may be able to contact an end or tip 250 of the device. When a user places the tip 250 of the device 200 and touches a surface, connection may be made not only with the surface of any object (e.g., a book, paper, wall, etc.), but also between the sensor 220 and the tip. When the sensor 220 and the tip 250 are in contact, the sensor 220 may generate a signal indicating that the device 100 is in use. The tip 250 of the device 100 may be any of a multitude of shapes, such as, for example, spherical, conical, triangular, rectangular, pyramidal or square-like.

With respect to the various types of sensors 220 that may be used, the switch may be a mechanical component that may click every time the tip 250 makes contact with the surface of an object.

The ball sensor may be a spherical element that may be placed within the inner portion of the case 200. As the tip 250 makes contact with the surface of an object, the tip 250 rises slightly into the case 200 and contacts the ball sensor, creating a closed circuit. When the closed circuit is in place, the device 100 is in use. If the tip 250 does not create contact with the ball sensor, an open circuit is created, and the device 100 is not in use.

The optical emitter detector may be a sensor that detects an optical signal emitted from an optical emitter. An optical emitter may be placed at the opposite end of the tip 250 and be triggered when a user touches the tip 250 of the device 100 with a surface. Upon the touching, a light may be emitted from the optical emitter, whereupon the light may be picked up by the optical emitter detector, indicating that the device 100 is in use.

The rocking ball switch may be similar to the ball sensor in that the rocking ball switch includes a spherical element. The rocking ball may be in contact with the side of the end of the tip 250. A switch may be positioned along the inner wall of the case 200 such that a gap exists between the rocking ball and switch. When the tip 250 contacts the surface of an object, the tip 250 may be pushed slightly up into the case 200, causing the rocking ball to come into contact with the switch to indicate that the device 100 is in use.

The accelerometer may be a module that can sense and/or measure the movement of the device. Any vibration from movement made on the device can be transmitted as data to an accelerometer reader to determine whether the device 100 is in use or not. Data presented may be in the form of graphical representations, such as charts with frequency modulations, pie charts, bar graphs, etc. A non-limiting example of an accelerometer that could be used in the device is the MMA7260Q made by Freescale Semiconductor.

Figure 3:
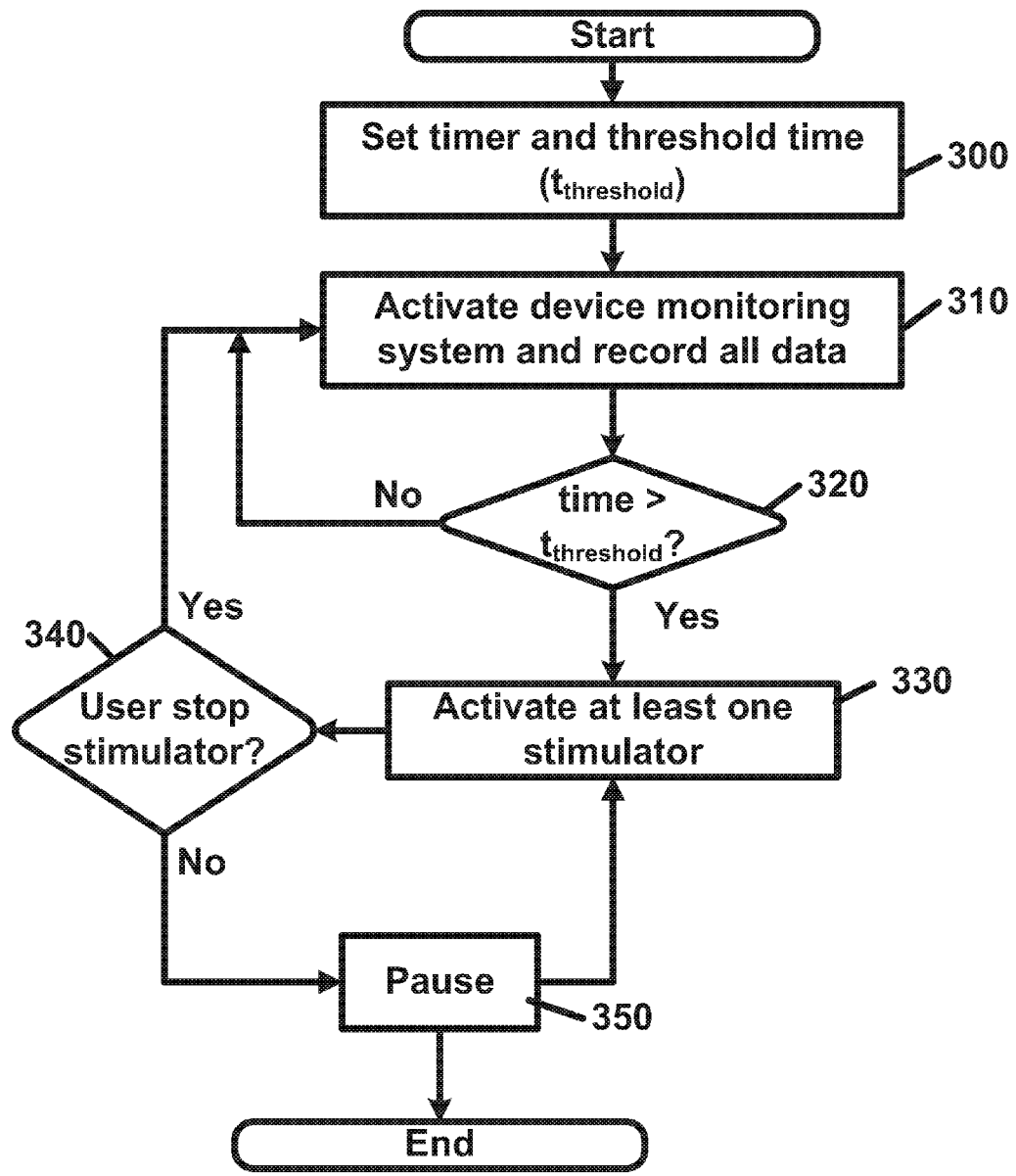
FIG. 3 is a diagram showing one implementation of operation of an attention assistance device, as per an aspect of an embodiment of the present invention.

As shown in FIG. 3, in operation of the device 100, the timer 130 may be set when the device 100 is first put to use, as shown in operation 300. In addition, the user may set a threshold time ($t_{threshold}$) as the time at which the stimulation unit 140 may be activated when no motion or use of the device 100 is detected after an initial start. At operation 310, once the device is put in use, the sensor may detect motion. At operation 320, when motion is no longer detected after a period of time (i.e., threshold time, such as 5 seconds, 30 seconds, 1 minute, etc.), the stimulation unit 140 may be activated at operation 330 to notify the user. Notification can be achieved by having the stimulation unit 140 send out a signal that alerts the user. The timing of the stimulation may vary and/or be adapted to the user's preferences, or the timing of the stimulation may be randomized. Once the signal is sent, the stimulation unit 140 may create the stimulating feature to alert the user that motion or use of the device 100 is not being detected.

At operation 340, the user may either manually stop the stimulation directly or by pressing a button 230, or the stimulation may stop automatically when the sensor 120 determines that motion or use of the device 100 has resumed. If motion or use of the device does not resume or the user does not stop the stimulation after a period of time (a pause at operation 350), the stimulation unit 140 may create the stimulating feature again to alert the user that motion or use of the device 100 is not being detected. This cycle may continue until the user stops the stimulation or motion or use of the device 100 is resumed. Alternatively, the cycle may repeat a particular number of times and then turn off or go to a sleep mode.

Figure 4:
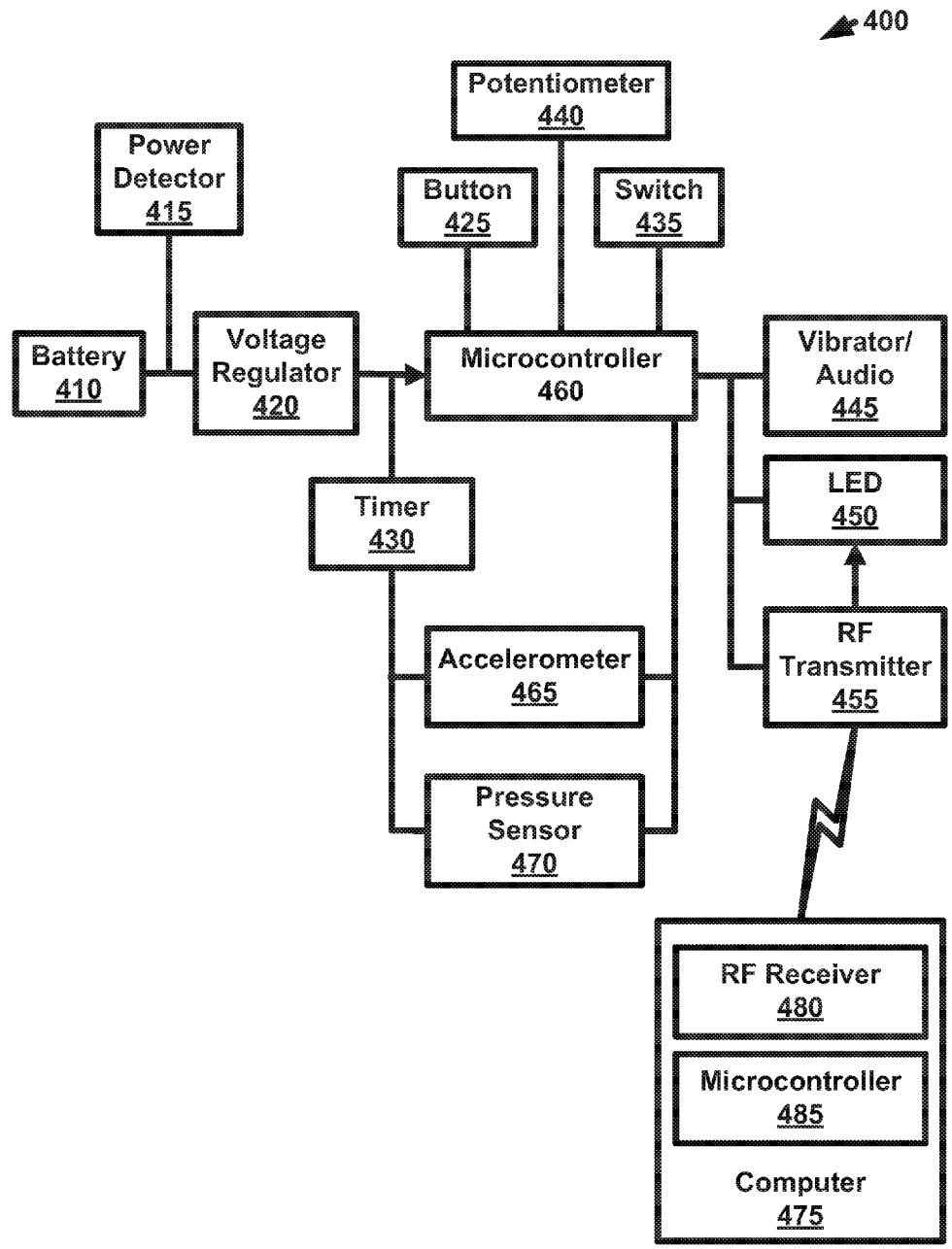
FIG. 4 is a block diagram showing an arrangement of an attention assistance system, as per an aspect of an embodiment of the present invention.

FIG. 4 illustrates additional features of an arrangement 400 of the device. In this arrangement, a battery 410 may be provided as a power source with a power detector 415 coupled to the battery 410 to monitor its usage life, and a voltage regulator 420 coupled to the battery 410 for regulating the voltage provided to components of the device. Additionally, the device may include a microcontroller 460 that functions to control the operation of the device and/or run program instructions. A non-limiting example of a microcontroller that could be used in the device is the ATMega328 made by Atmel Corporation. A button 425 and switch 435 may be provided to obtain input from a user to power the device on and off or put the device in sleep mode, as well as adjusting various settings or stopping the stimulation. An accelerometer 465 may be included for sensing motion of the device, while a pressure sensor 470 may also be included for sensing use of the device when the tip of the device contacts a surface.

In this arrangement, the stimulation unit may include two or more stimulators as vibrator/audio 445 and illumination source, LED 450. When two or more stimulators are incorporated, the microcontroller 460 of the device may randomly change the type of stimulation based upon the previous performance. A reason for providing such randomization is to prevent the user from becoming sensitized to the stimulus. Further, the device may include an RF transmitter 455 as a wireless communication unit for transmitting data relating to the use of the device to a remote computer 475 or equivalent computer hardware. The computer or computer-equivalent hardware may have a processor and the ability to display or print out data and/or results and may further include memory storage capacity, a keyboard, a mouse, an image module capable of displaying data, etc. The computer 475 may include an RF receiver 480 to receive the RF signal transmitted by the RF transmitter 455 of the device, as well as a microcontroller 485 to convert the signal and analyze and/or display the data at the remote computer 475. Alternatively, the wireless interface may be Bluetooth, IEEE 802.11 technology, RF, 3G, 4G, mobile telecommunications wireless standards, or similar wireless technology. A non-limiting example of an RF transmitter and receiver that can be used in the device are the MO-SAWR-AS315M transmitter and MO-RX3400-A315M receiver both made by Holy Stone Enterprise.

Figure 5:
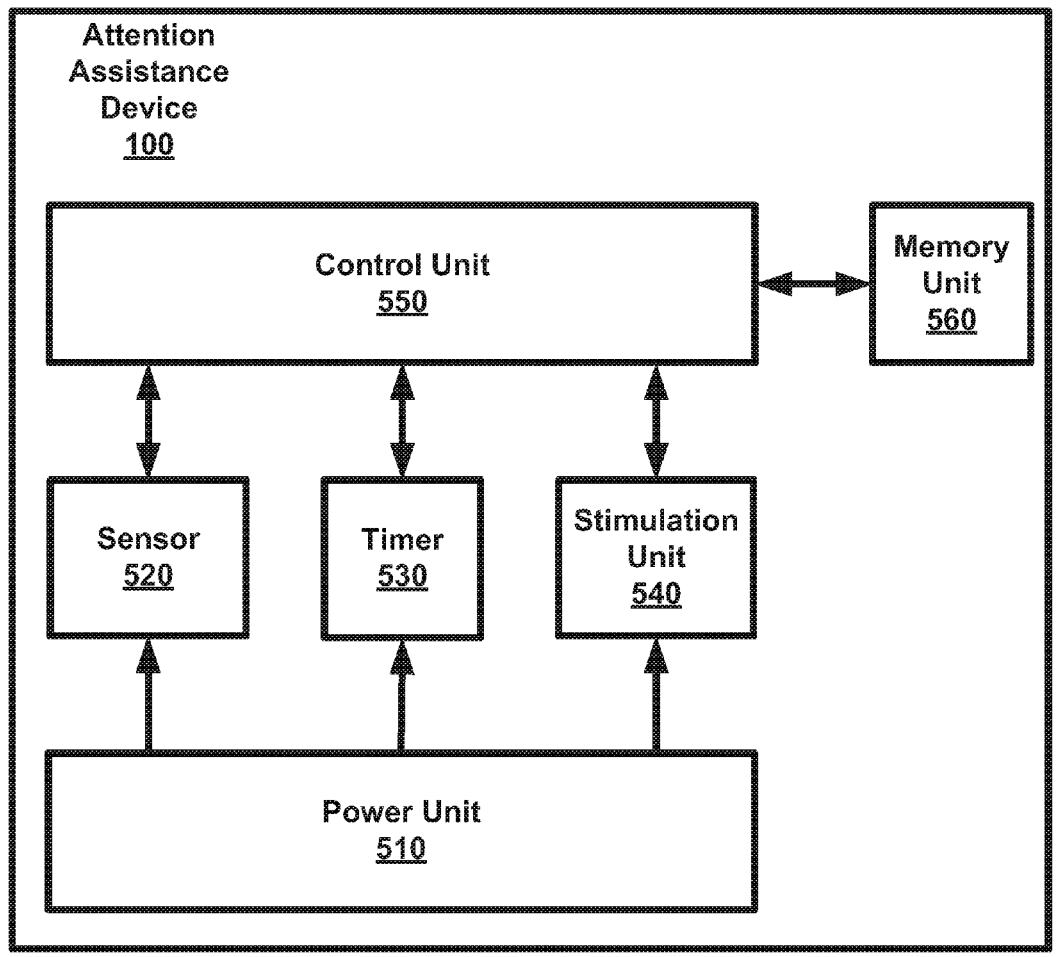
FIG. 5 is a block diagram showing an arrangement of an attention assistance device, as per an aspect of an embodiment of the present invention.

FIG. 5 shows a block diagram of an alternative arrangement of the device 100. Similar to the device shown in FIG. 1, the device 100 may include a sensor 520, a timer 530, and a stimulation unit 540, in addition to a power unit 510 as a source for providing power to the various components of the device. Additionally, as shown in FIG. 5, the device 100 may include a control unit 550 and a memory unit 560. The memory unit 560 may be any type of storage device, including but not limited to RAM, ROM, etc. The memory unit may store program instructions or software for the operation of the device 100 that are read and run by the control unit 550. Further, the control unit 550 may be used for controlling the various operations of the device 100 and may write data relating to the use of the device 100 to the memory unit 560. The data relating to the use of the device or performance of the user may include, for example, activity sensor output history, stimulation unit activation frequency, timer history, battery life, and type of stimulation used.

Figure 6:
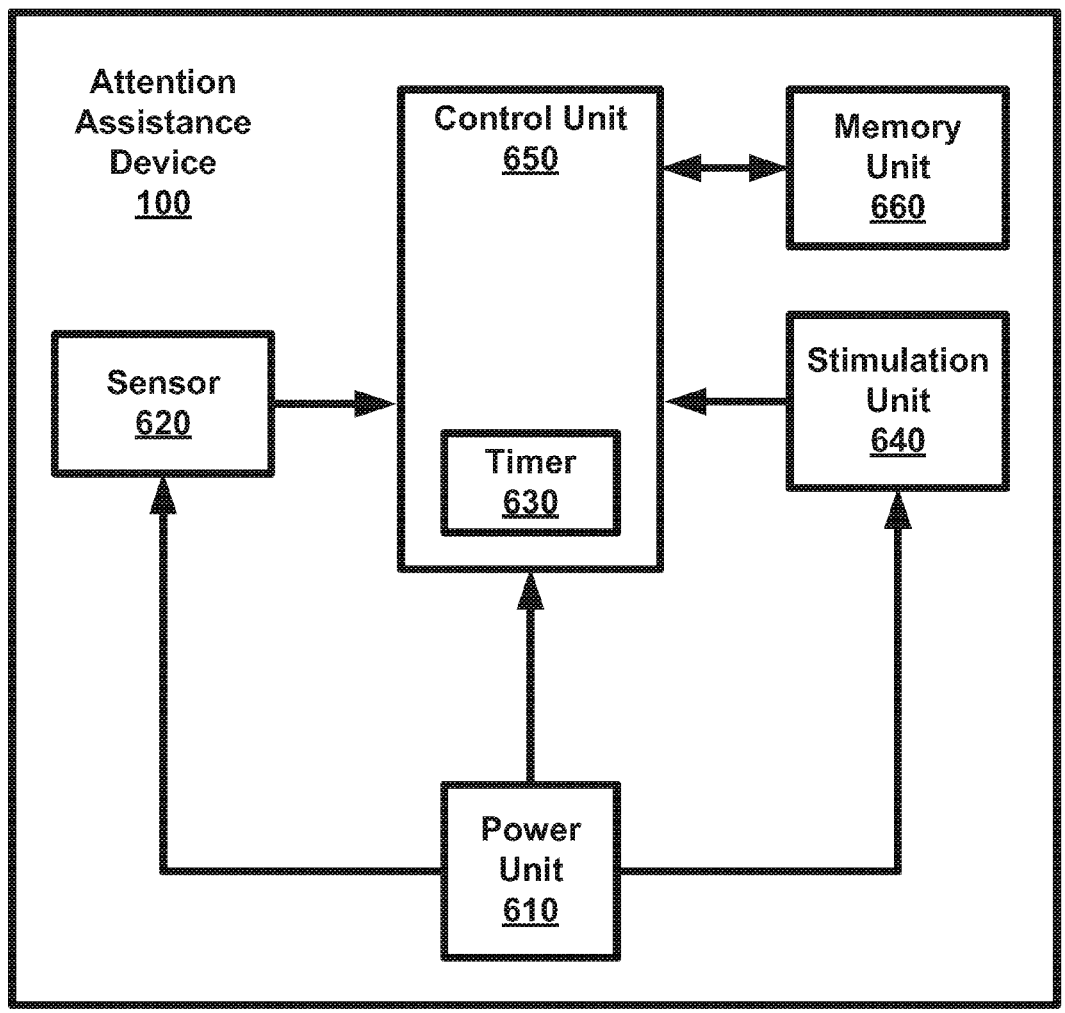
FIG. 6 is a block diagram showing an arrangement of an attention assistance device, as per an aspect of an embodiment of the present invention.

The timer 530 can be part of the device 100, as shown in FIG. 5. Alternatively, as shown in FIG. 6, the timer 630 may be incorporated into the software run by the control unit 650 of the device. In the arrangement shown in FIG. 5 and FIG. 6, where the device includes a control unit, the timer and threshold time may be adaptively set based on the data accumulated regarding the performance of the user. Alternatively, the device may be connected to a computer or equivalent computer hardware so that the user may set the timer. Similar to the arrangement shown in FIG. 5, the arrangement shown in FIG. 6 may also include a power unit 610, a sensor 620, a stimulation unit 640, and a memory unit 660, in addition to the timer 630 and control unit 650 discussed above.

Figure 7:
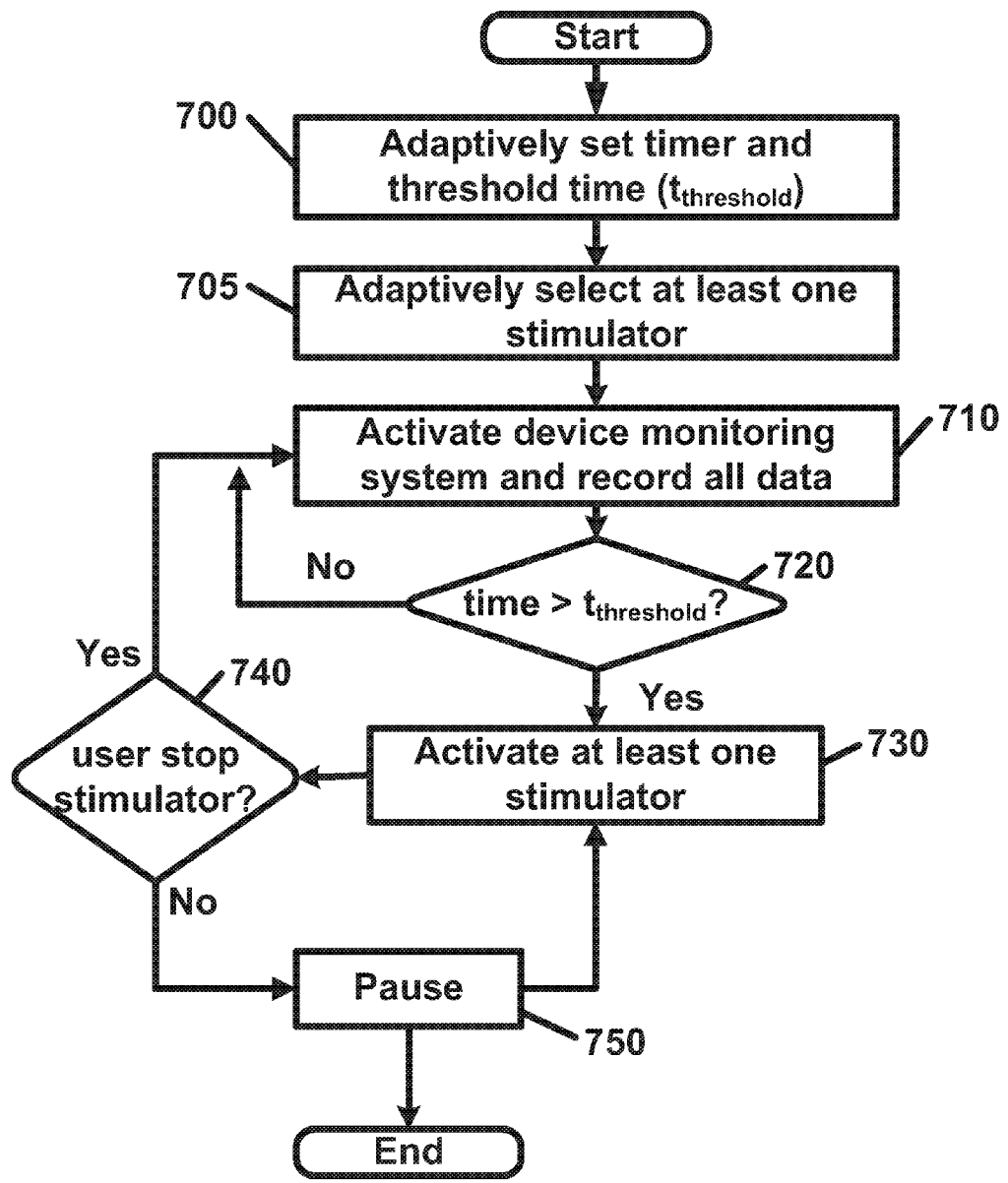
FIG. 7 is a diagram showing one implementation of the operation of an attention assistance device, as per an aspect of an embodiment of the present invention.

The operation of the device that is shown in the diagram in FIG. 7 is similar to that discussed above with respect to FIG. 3 except that in this example, for the operation 700 of FIG. 7, the timer and threshold time are adaptively set based on the data relating to the use of the device. Additionally, at least one stimulator may be adaptively selected in operation 705 based on the data relating to the use of the device. In this way, the device can automatically adjust the threshold time used for alerting the user of inactivity of the device based on how well the user is performing. Similarly, the stimulation can automatically be adjusted and varied based on the user's performance and/or the stored data relating to the use of the device.

Figure 8:
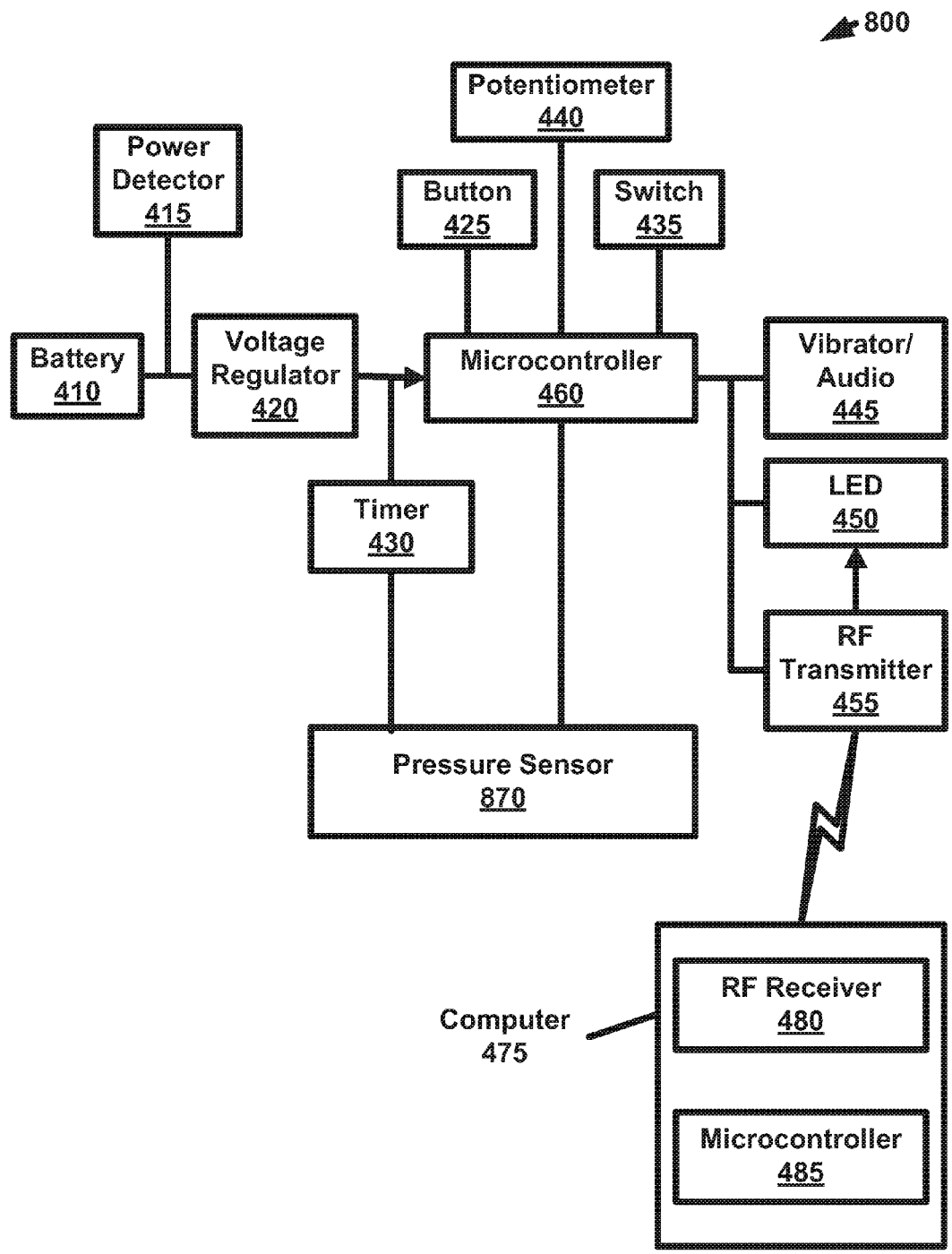
FIG. 8 is a block diagram showing an arrangement of an attention assistance system, as per an aspect of an embodiment of the present invention.
Figure 9:
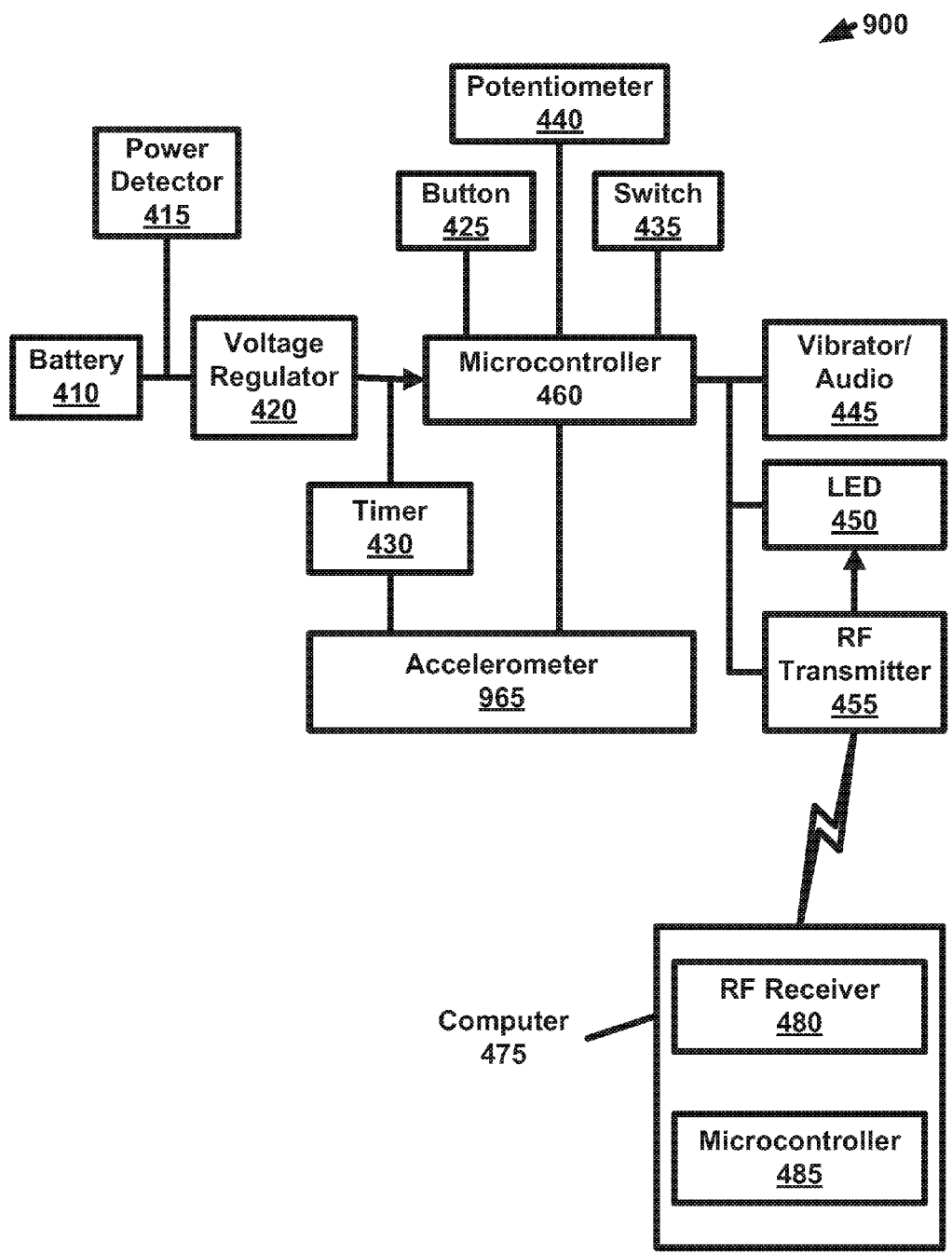
FIG. 9 is a block diagram showing an arrangement of an attention assistance system, as per an aspect of an embodiment of the present invention.

Additional arrangements of the attention assistance device are shown in FIGS. 8-13. These arrangements are variations of the device 400 shown in FIG. 4, with like components being like-numbered. The arrangement shown in FIG. 8 is similar to device 400 of FIG. 4 except in this example, device 800 has a pressure sensor 870 for sensing use of the device when the tip of the device contacts a surface, without an accelerometer. The arrangement shown in FIG. 9 is similar to device 400 of FIG. 4 except in this example, device 900 has an accelerometer 965 for sensing motion of the device, without a pressure sensor.

Figure 10:
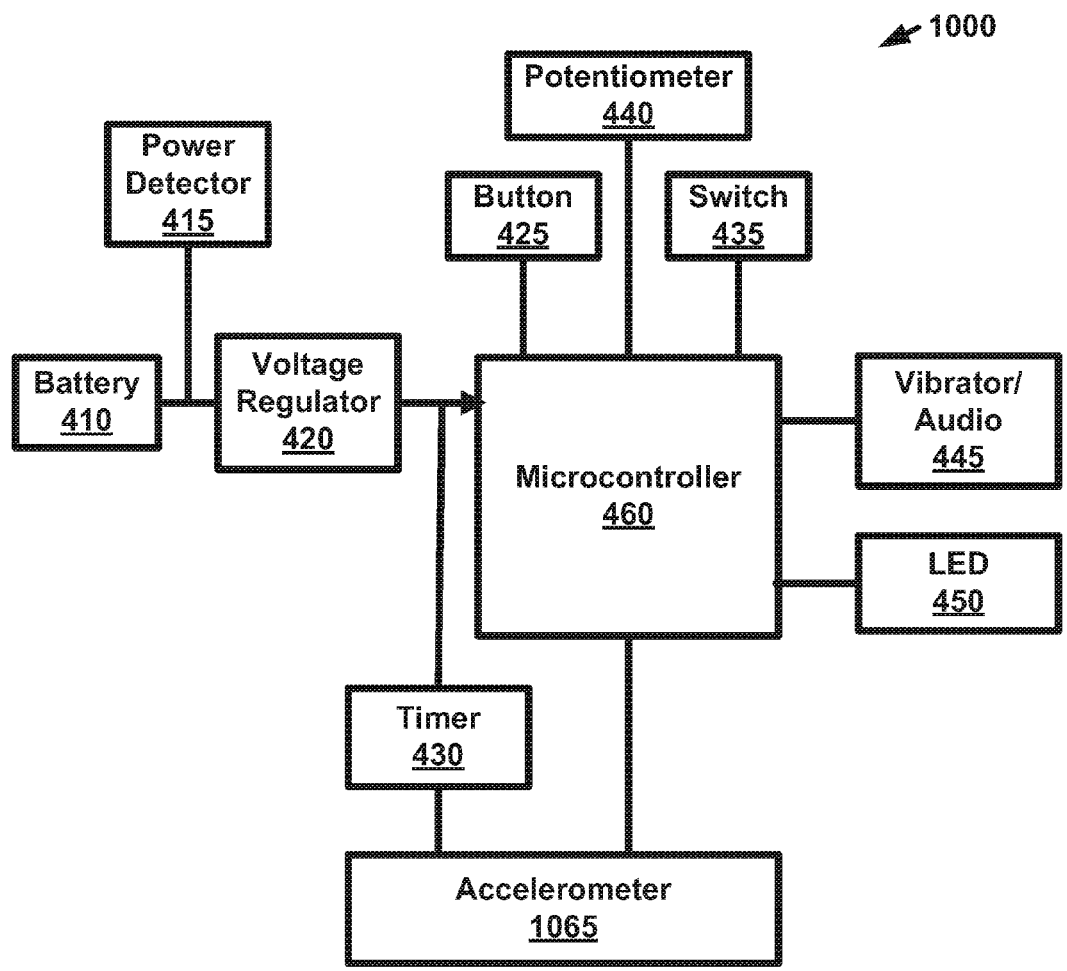
FIG. 10 is a block diagram showing an arrangement of an attention assistance device, as per an aspect of an embodiment of the present invention.
Figure 11:
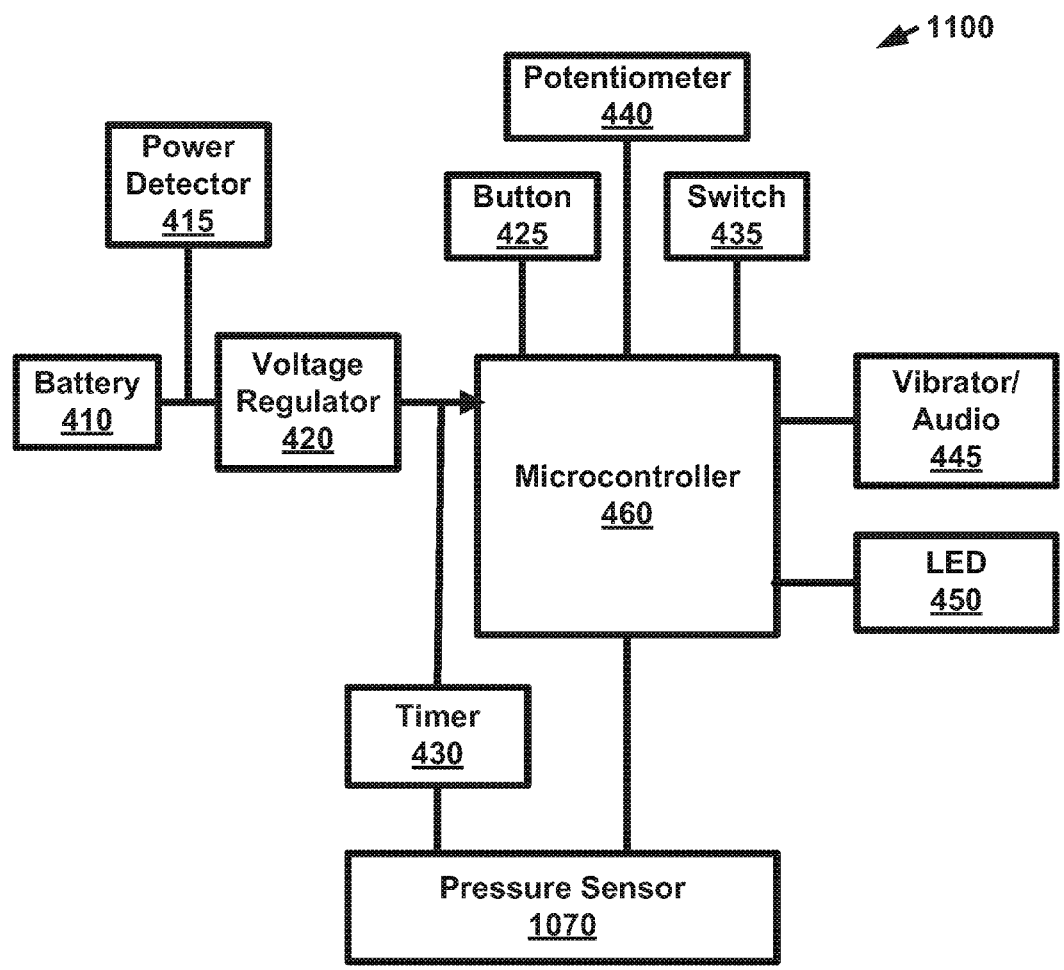
FIG. 11 is a block diagram showing an arrangement of an attention assistance device, as per an aspect of an embodiment of the present invention.
Figure 12:
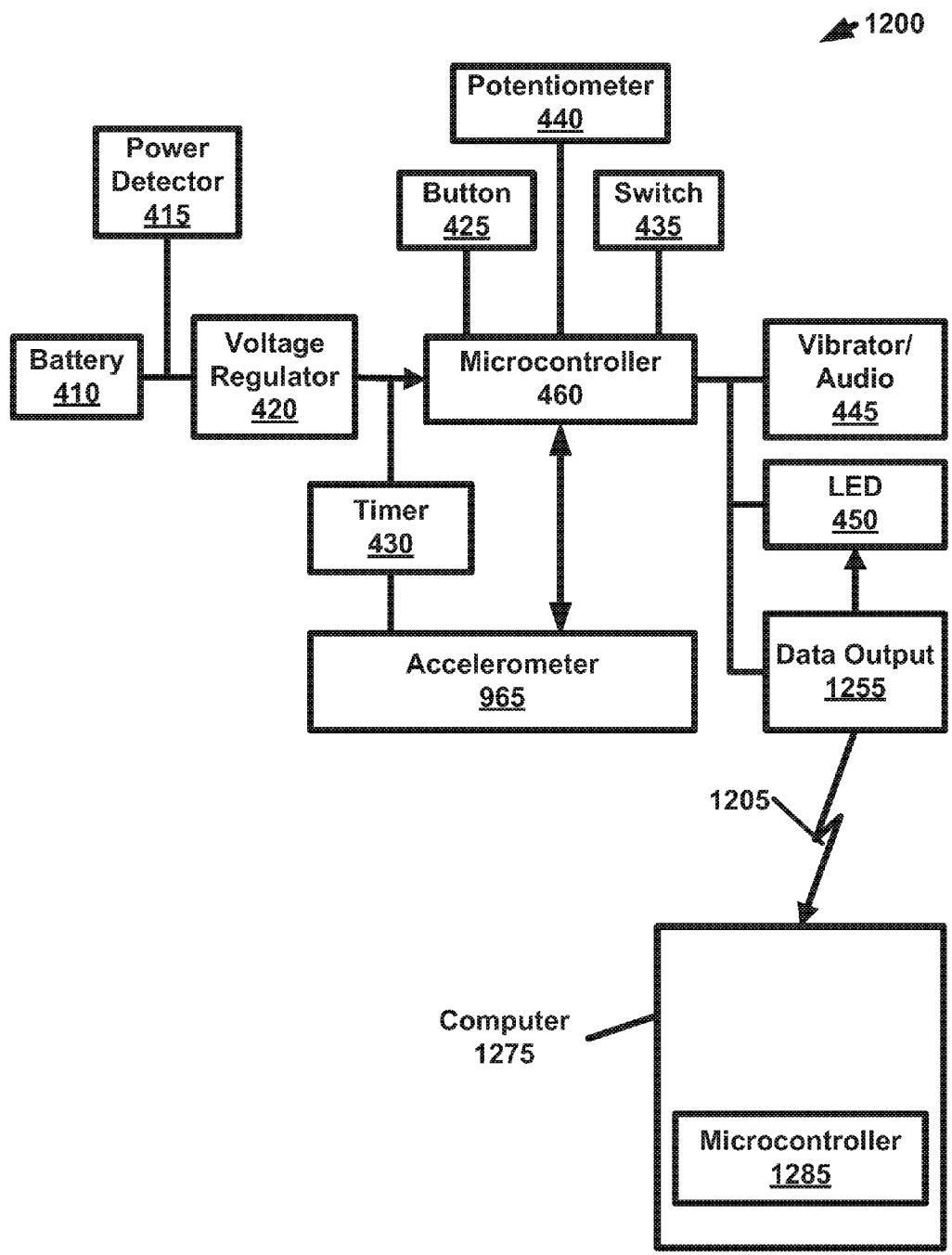
FIG. 12 is a block diagram showing an arrangement of an attention assistance system, as per an aspect of an embodiment of the present invention.
Figure 13:
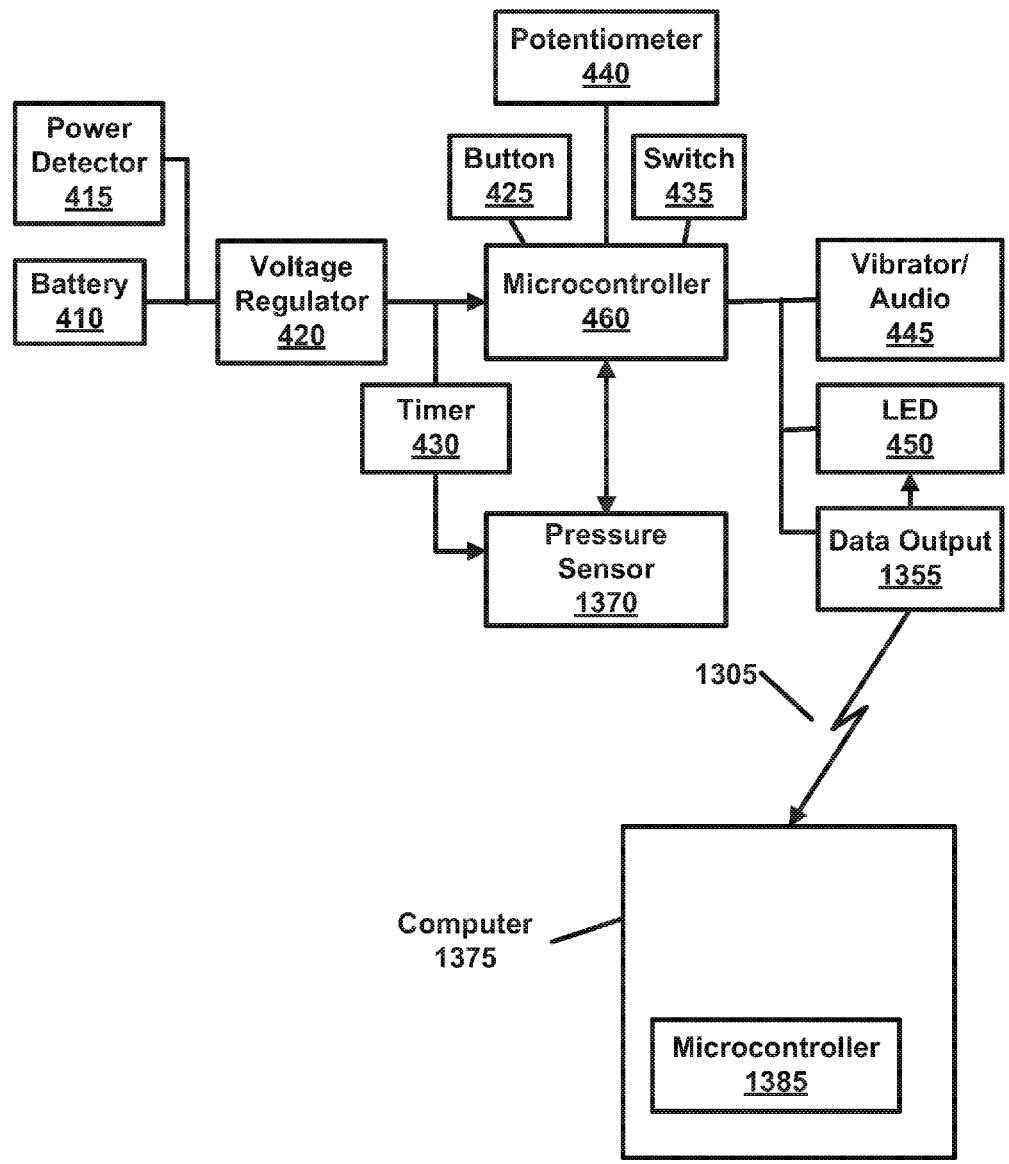
FIG. 13 is a block diagram showing an arrangement of an attention assistance system, as per an aspect of an embodiment of the present invention.

The arrangement shown in FIG. 10 is similar to device 400 of FIG. 4 except in this example, device 1000 has an accelerometer 1065 for sensing motion of the device, without a pressure sensor. Another difference from device 400 is that the arrangement of device 1000 shown in FIG. 10 lacks a communication interface, thereby reducing costs of production of the device 1000. Similarly, the arrangement shown in FIG. 11 is similar to device 400 of FIG. 4 except in this example, device 1100 has a pressure sensor 1170 for sensing use of the device when the tip of the device contacts a surface, without an accelerometer. Also, the arrangement shown in FIG. 11 lacks a communication interface, thereby reducing costs of production of the device The arrangement shown in FIG. 12 is similar to device 400 of FIG. 4 except in this example, device 1200 has an accelerometer 1265 for sensing motion of the device, without a pressure sensor. Another difference from device 400 is that the arrangement of device 1200 shown in FIG. 12 may include a wired interface 1205 for transmitting data relating to the use of the device from a data output 1255 to a remote computer 1275 or equivalent computer hardware. The computer 1275 may include a microcontroller 1285 to convert the received data and analyze and/or display the data at the remote computer 1275. The wired interface 1205 with data output 1255 may be, for example, USB, serial port, parallel port, modem or phone line, Ethernet, or FireWire. Similarly, the arrangement shown in FIG. 13 similar to device 400 of FIG. 4 except in this example, device 1300 has a pressure sensor 1370 for sensing use of the device when the tip of the device contacts a surface, without an accelerometer. Also, like the arrangement shown in FIG. 12, the arrangement of FIG. 13 may include a wired interface 1305 for transmitting data relating to the use of the device from a data output 1355 to a remote computer 1375 or equivalent computer hardware. The computer 1375 may include a microcontroller 1385 to convert the received data and analyze and/or display the data at the remote computer 1375. Again, the wired interface 1305 with data output 1355 may be, for example, USB, serial port, parallel port, modem or phone line, Ethernet, or FireWire.

The attention assistance device may help a medical provider (e.g., doctor, nurse, chiropractor, emergency medical service provider, physician, therapist, etc.) analyze the activities of patients with ADD, ADHD, or other attention disorders by, for example, monitoring how often attention is lost or how often some stimulus is needed. The medical providers may receive data from the attention assistance device remotely or directly from the attention assistance device. The data may be used by a medical provider to provide adequate medical treatment or advice to users, especially those with attention-deficit disorders. The data may include one or more of, for example, the number of detected inattention episodes, performance of stimulators, the time it took to regain attention (sensor redetecting attention assistance device usage) after being stimulated, activity sensor output history, stimulation unit activation frequency, timer history, battery life, date, time, progress indicator and type of stimulation used.

Whether the focus is a task with writing, reading, or presenting a subject matter, the attention assistance device is expected to help a person with ADD, or other attention disorder such as a reading disorder, dyslexia, visual disorder, auditory disorder stay on track with the task at hand. Furthermore, arrangements of the attention assistance device make it inconspicuous (such as appearing like a regular pen, pointer, tablet or the like) such that the user may use the device in public without others knowing it is an attention assistance device to avoid potential embarrassment of the user.

Further, the attention assistance device may be multi-tipped. Where the attention assistance device is multi-tipped, one tip may be used as the attention assistance device tip and the other tip may be used as a writing instrument. Either or both of the tips may have a writing source storage section that may have an ink source, lead source, crayon source, or highlighter source.

An automatic on/off/sleep mode option may be set by the user. Because the stimulator may be activated once the attention assistance device is no longer detected in use, the automatic on/off/sleep mode option may override the stimulator after a certain period of time. For example, after 30 seconds or 1 minute of stimulation, the attention assistance device may automatically be turned off or pause (enter sleep mode). If the attention assistance device enters sleep mode, the attention assistance device may wake up after a certain time that may be set by the user (e.g., 2 minutes) by having the stimulator send out another stimulus. Such stimulus may be the same stimulus prior to entering the sleep mode or be a different stimulus.

Another example of the attention assistance device put to use, as outlined in FIG. 7 may be as follows: adaptively set timer ($t_0$) and threshold time ($t_{threshold}$) at 700, and adaptively select at least one stimulator at 705. Time $t_0$ may mark the start of usage of the attention assistance device. Threshold time $t_{threshold}$ is the time (which may be set by the user or may be the default time setting) at which a level of inactivity is no longer tolerated, thus causing a stimulator to be activated. If time surpasses this threshold time at 720, at least one stimulator may be activated at 730. If not, then the attention assistance device may continue to be in use at 710. If a stimulator is activated, the next aspect is whether the user stopped the stimulator at 740. If so, then the attention assistance device may be continued for use at 710. If not, then there may be either a pause 750 or the attention assistance device may shut down automatically. If there is a pause 750, the same or another stimulator may be activated at 730 after a certain period of time (e.g. 1 minute later, etc.).

In an alternative implementation of the attention assistance device, the sensor, for example an accelerometer, determines use of the device from a user's movement of the device from one point on a page or surface to another point on the page or surface. For example, the sensor may determine the device is in use based upon a user moving the device from the left-most or right-most side of a page or surface to the opposite right-most or left-most side of the page or surface, such as moving from the end of a line of text to the start of another line of text.

Figure 14:
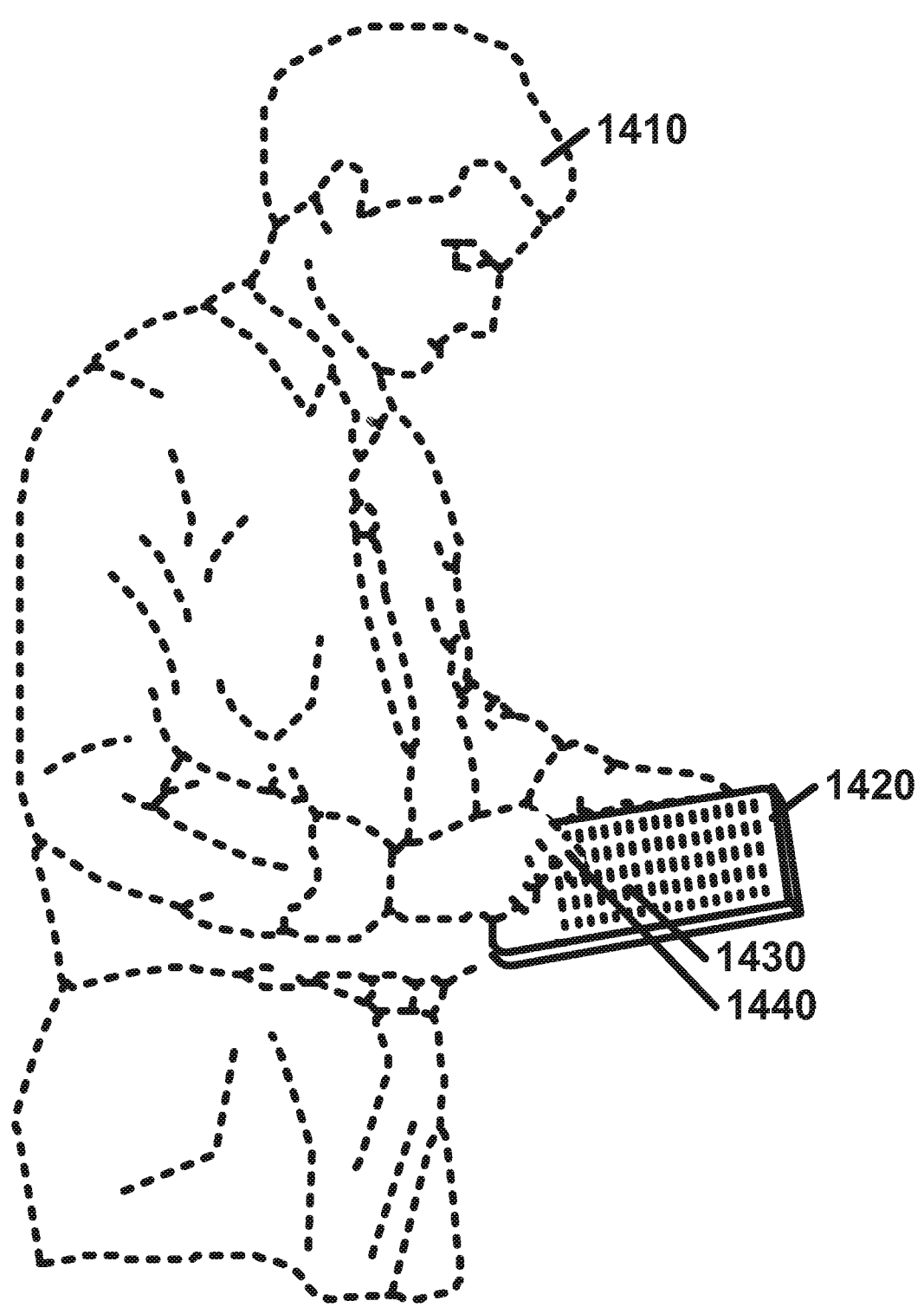
FIG. 14 is an illustration of a person using an attention assistance device, as per an aspect of an embodiment of the present invention.
Figure 15:
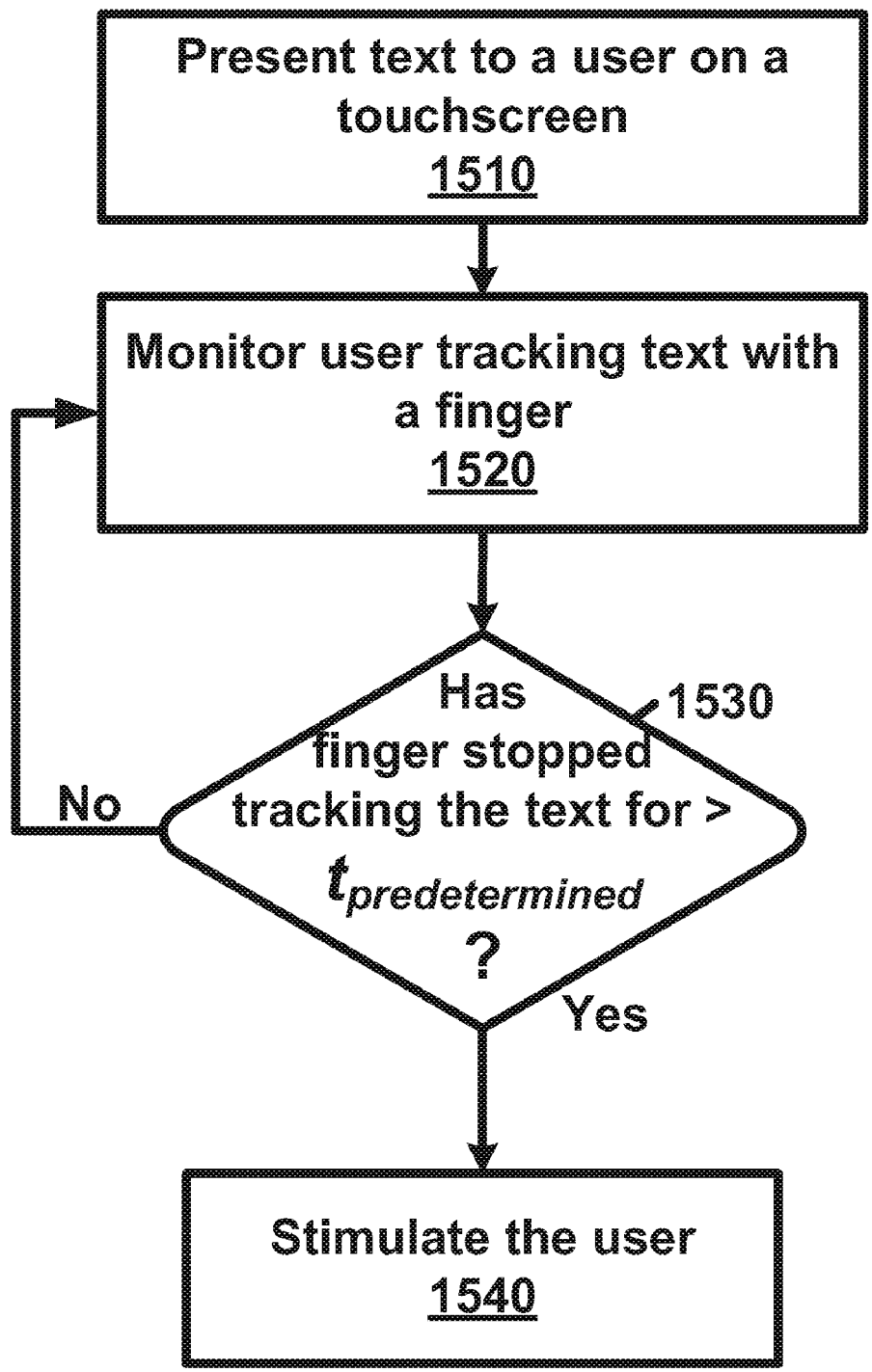
FIG. 15 is a flow diagram that illustrates a method of an attention assistance process, as per an aspect of an embodiment of the present invention.

Reference will now be made to FIG. 14 and FIG. 15 to explain an example embodiment of the present invention that uses an electronic device such as an electronic tablet or the like. FIG. 14 is an illustration of a person 1410 using an attention assistance device 1420, as per an aspect of an embodiment of the present invention. FIG. 15 is a flow diagram that illustrates a method of an attention assistance process, as per an aspect of an embodiment of the present invention.

As illustrated, in this example embodiment, a tangible non-transient computer readable medium contains a multitude of computer readable instructions that when executed by one or more processors causes the one or more processors to perform an attention assistance process. At 1510, text 1430 is presented to a user 1410 on electronic tablet 1420. User 1410 tracking the text 1430 using a finger 1440 (or other appendage, device or the like) may be monitored at 1520. The user 1410 may be stimulated at 1540 when the finger 1440 stops tracking the text 1430 for a predetermined period of time (see 1530). The electronic tablet 1420 may include a touchscreen. In this embodiment, the text 1430 may be presented on the touch screen and the tracking monitored using the input capability of the touchscreen. The stimulating (1540) may include a mechanism configured to alert user 1410 that they may have lost attention. Examples of such mechanisms include: vibration, sound, light, flashing of a touchscreen, an electric pulse, a combination thereof, or the like.

To assist the user 1410, the text may be emphasized as the user 1410 tracks the text 1430 using the finger 1440. One example of emphasis is to enlarge the word(s) as they are being tracked. Another example of emphasis would be to change the characteristics of the word(s) as they are being tracked. Example characteristics may include the font, the color, whether the word(s) are underlined, italicized, shadowed or the like.

Figure 16B:
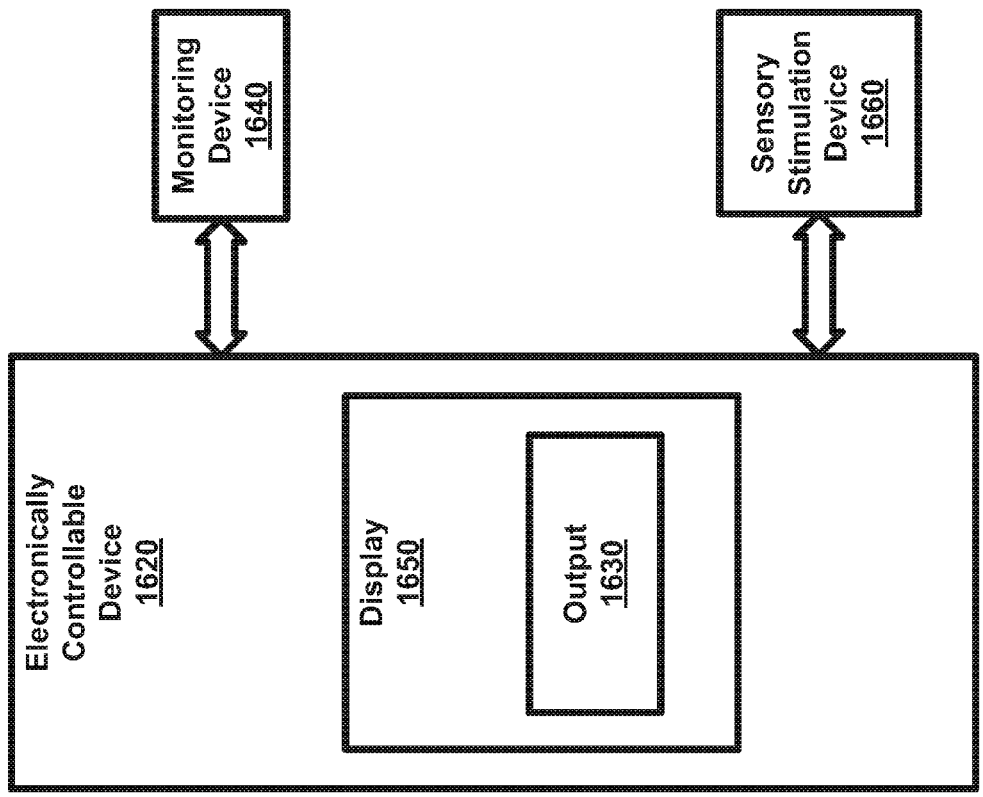
FIG. 16A and FIG. 16B are block diagrams showing two example configurations of an attention assistance apparatus, as per aspects of an embodiment of the present invention.
Figure 16A:
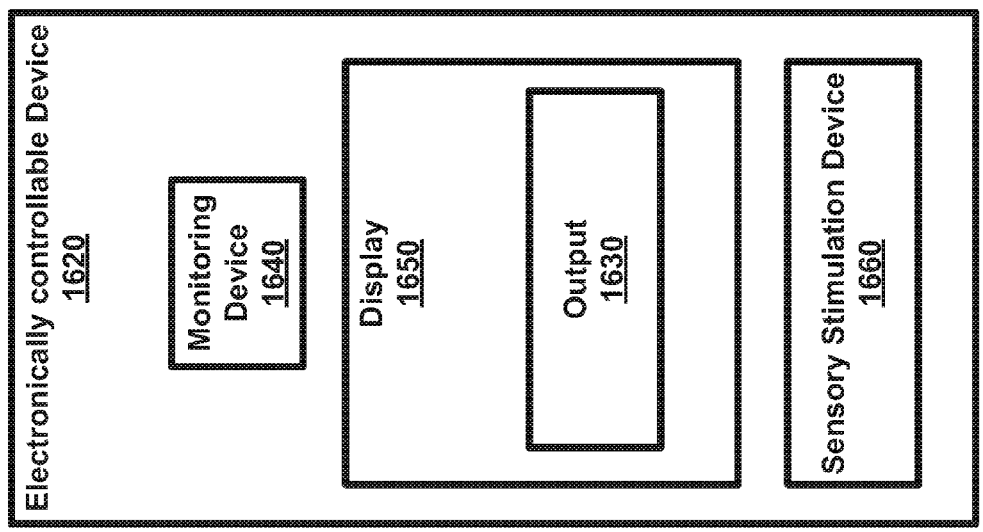

FIG. 16A and FIG. 16B are block diagrams showing two example configurations of an attention assistance apparatus, as per aspects of an embodiment of the present invention. Both of these illustrated example apparatuses include an electronic device 1620, a monitoring device 1640 and a sensory stimulating device 1660. A difference between these two example embodiments is the location of the monitoring device 1640 and the sensory stimulation device 1660. In FIG. 16A, these elements are internal to the electronically controllable device 1620 and in FIG. 16B, these elements are external to the electronically controllable device 1620. One skilled in the art will recognize that other example embodiments may include different combinations of these and other elements (e.g. display 1650) being located in and out of the electronic controllable device 1620. For example, an external display 1650 may be used with electronic controllable device 1620. This may be useful, when, for example, the electronic controllable device 1620 is a netbook, smart phone or other small device and it is desired to work with a larger display.

Examples of electronic device 1620 include: computer(s), laptop(s), phone(s), eReader(s), television(s), system(s) having embedded processor(s), PDA(s), electronic tablet(s), combinations thereof or the like. Electronic device 1620 may be configured to present an output 1630 using devices such as an electronically modifiable display 1650. Output 1630 may be configured to be tracked by a user. In FIG. 16A and FIG. 16B, the output 1630 may be presented visually on a display 1650. However, it is envisioned that with some embodiments, the output may be presented on other devices also configured to stimulate other senses such as hearing, touch, or the like.

When the output 1630 is visual, the output 1630 may be presented using a monitor, a projector, light emitting device, light reflective device, combinations thereof or the like. An example of visual output 1630 is text. Other visual output 1630 may include graphical shapes, images, or the like.

When the output 1630 is acoustic, the output 1630 may be presented using a speaker, a shaker, a headphone, combinations thereof or the like. Examples of acoustic output 1630 include sounds such as music, object sounds, vocalizations or the like.

When the output 1630 is tactile, the output 1630 may be presented using a temperature modifiable device, a braille display, a tactile display a controllable vibrator, combinations thereof or the like. A braille display is a tactile device consisting of a row of special 'soft' cells that have pins controlled to move up and down to display braille characters. Tactile displays have been demonstrated by the National Institute Standards and Technology (NIST). Examples of tactile output 1630 include braille, temperature, shapes or the like.

Monitoring device 1640 may be configured to observe a user tracking the output 1630. The monitoring device 1640 may be configured to observe may different indicators of attention such as: brainwaves, body movement, finger movement, pulse, blood pressure, perspiration, respiration, eye movement, stylus movement, foot movement, mouse movement, computer keyboard use, oral emissions, cursor key activation, combinations of the above, or the like. According to some embodiments, normal computer input/out devices may be monitored. According to some embodiments, biological monitoring equipment may be utilized. Cameras may be used to monitor some of the attention indicators such as eye movement, body movements, combinations thereof or the like.

Sensory stimulating device 1660 may be configured to stimulate a user when the tracking falls below an attention threshold. In some embodiments, the attention threshold may be a period of time between user interactions with the output 1630. Other attention thresholds may also be implemented. For example an attention threshold may be used that measures a users ability to interact with the output 1630 such as a time to answer a question, time spent over particular words or concepts, accuracy in tracking the output, or the like. Examples of sensory stimulation devices include: vibrator(s), speaker(s), light emitting device(s), display(s), LED(s), electrode(s), combinations thereof or the like.

Figure 17:
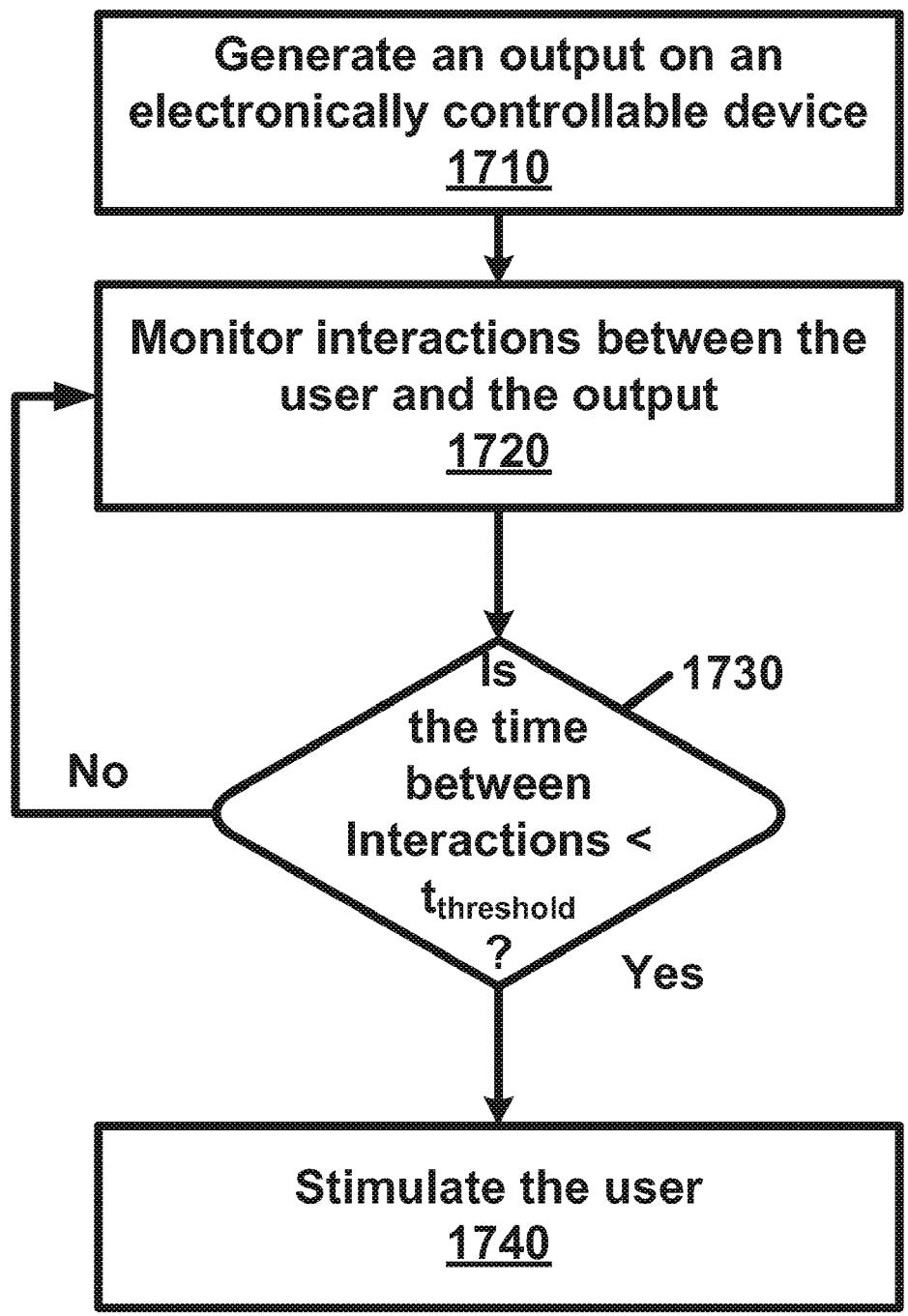
FIG. 17 is a flow diagram that illustrates a method of an attention assistance process, as per an aspect of an embodiment of the present invention.

FIG. 17 is a flow diagram that illustrates an example method of an attention assistance process, as per an aspect of an embodiment of the present invention. This and other attention assistance and monitoring processes may be implemented using non-transient tangible computer readable medium containing a multitude of computer readable instructions that when executed by one or more processors, causes the one or more processors to perform an attention assistance and/or monitoring process. At 1710, an output configured to be tracked by a user on an electronic device may be presented. A user tracking the output may be actively monitoring at

1720. The user may be stimulated at 1740 when the tracking falls below an attention threshold (see 1730). According to some embodiments, stimulating content may be added to the output. Examples of stimulating content include prompts, flashing, sound, combinations thereof or the like.

According to some embodiments, the output may be text. As described earlier, output is not limited to visual outputs. For example the output may be configured to present output acoustically, tactilely, combinations thereof or the like.

To assist some users, the output may be narrated as it is tracked. This may help blind users, users with disabilities such as dyslexia, or the like. Physical grooves on a device may help the user align their tracking. For example, a blind person may use a physical grove to align their tracking movement as they move a finger over the content.

According to embodiments, examples of electronic device(s) are: computer(s), laptop(s), phone(s), smart phone(s), eReader(s), television(s), system(s) incorporating embedded processor(s), PDA(s), electronic tablet(s), combinations of the above or the like. According to embodiments, examples of elements that may be used with or part of electronic device(s) include: display(s), touchscreen(s), ePaper display(s), computer mice, camera(s), keyboard(s), stylus(es), computer(s), wireless communications device(s), combinations of the above, or the like. The display and monitoring device may be integrated. For example, a touch screen may be used that integrates both touch feedback as well as the display. Many computers include both a display and camera. It is envisioned that other embodiments may use other integrated devices.

Embodiments of the present invention may be configured to collect statistical data related to users interacting with content using the monitoring. Examples of the statistical data includes, but is not limited to: a reading speed statistic(s), reading speed statistic(s) associated with parts of the output(s), reading statistic(s), stimulation statistic(s), combinations of the above, or the like. Embodiments of the present invention may collect statistics that could be used by teachers, therapist, or the like. For example, statistics may be used to understand how well subjects understand questions in an exam by monitoring their response time over parts of the question. Similarly, data may be collected about time spent while reading specific words in a document. This kind of data may be aggregated over a multitude of users to study or determine the efficacy of content.

Embodiments of the present invention may be adaptive or otherwise dynamic. For example, when the attention threshold is a period of time, the time period may be configured to change. In the case of stimulation, examples of changes may include the period, frequency and type of stimulation. These changes may be based upon collected interaction statistic(s). Additionally, the changes may have a random component.

In this specification, "a" and "an" and similar phrases are to be interpreted as "at least one" and "one or more." References to "an" embodiment in this disclosure are not necessarily to the same embodiment.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e hardware with a biological element) or a combination thereof, all of which are behaviorally equivalent. For example, modules may be implemented using computer hardware in combination with software routine(s) written in a computer language (such as C, C++, Fortran, Java, Basic, Matlab or the like) or a modeling/simulation program such as Simulink, Stateflow, GNU Octave, or LabVIEW MathScript. Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

The disclosure of this patent document incorporates material which is subject to copyright protection. The copyright owner has no objection to the facsimile reproduction by anyone of the patent document or the patent disclosure, as it appears in the Patent and Trademark Office patent file or records, for the limited purposes required by law, but otherwise reserves all copyright rights whatsoever.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the above explanation includes an example of assisting a user to pay attention while reading text presented to a user on a touchscreen. However, one skilled in the art will recognize that there can be many other embodiments of the invention. For example, an embodiment of the present invention could include helping a musician maintain attention using a device that requires trackable interactions with musical notation, metronome beats, or the like.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A non-transient computer readable medium containing a multitude of computer readable instructions that when executed by one or more processors causes the one or more processors to perform a process comprising:
  a) presenting text to a user on a touchscreen;
  b) monitoring the user tracking the text using a finger; and
  c) stimulating the user when the finger stops tracking the text for a predetermined period of time.

2. The non-transient computer readable medium according to claim 1, wherein the stimulating includes at least one of the following:
  a) vibration;
  b) sound;
  c) light;
  d) flashing of the touchscreen;
  e) an electric pulse; or
  f) a combination thereof.

3. The non-transient computer readable medium according to claim 1, wherein the text is emphasized as the user tracks the text using the finger.

4. An apparatus, comprising:
  a) an electronic device configured to present an output configured to be tracked by a user;
  b) a monitoring device configured to observe the user tracking the output;
  c) a sensory stimulating device configured to stimulate the user when the tracking falls below an attention threshold.

5. The apparatus according to claim 4, wherein the output is text.

6. The apparatus according to claim 4, wherein the electronic device includes an electronically modifiable display.

7. The apparatus according to claim 4, wherein the electronic device is one of the following:
  a) a computer;
  b) a laptop;
  c) a phone;
  d) an eReader;
  e) a television
  f) a system having an embedded processor;
  g) a PDA; or
  h) an electronic tablet.

8. The apparatus according to claim 4, wherein the monitoring device is configured to observe at least one of the following:
  a) brainwaves;
  b) body movement;
  c) finger movement;
  d) a pulse;
  e) blood pressure;
  f) perspiration;
  g) respiration;
  h) eye movement;
  i) stylus movement;
  j) foot movement;
  k) mouse movement;
  l) computer keyboard use;
  m) a voice;
  n) cursor key activation; or
  o) a combination of the above.

9. The apparatus according to claim 4, wherein the sensory stimulation device includes at least one of the following:
  a) a vibrator;
  b) a speaker;
  c) a light emitting device;
  d) a display;
  e) an LED;
  f) an electrode; or
  g) a combination thereof.

10. An non-transient computer readable medium containing a multitude of computer readable instructions that when executed by one or more processors causes the one or more processors to perform a process comprising:
  a) presenting output configured to be tracked by a user on an electronic device;
  b) actively monitoring the user tracking the output; and
  c) stimulating the user when the tracking falls below an attention threshold.

11. The non-transient computer readable medium according to claim 10, further including adding stimulating content to the output that tracks the user tracking the output.

12. The non-transient computer readable medium according to claim 10, wherein the output is text.

13. The non-transient computer readable medium according to claim 10, further including narrating the tracked output.

14. The non-transient computer readable medium according to claim 10, wherein the electronic device includes at least one of the following:
  a) a display;
  b) touchscreen;
  c) an ePaper display;
  d) a mouse;
  e) a camera;
  f) a keyboard;
  g) a stylus;
  h) a computer;
  i) a wireless communications device; or
  j) a combination of the above.

15. The non-transient computer readable medium according to claim 10, wherein the electronic device is one of the following:
  a) a computer;
  b) a laptop;
  c) a phone;
  d) an eReader;
  e) a television;
  f) a system having an embedded processor;
  g) a PDA; or
  h) an electronic tablet.

16. The non-transient computer readable medium according to claim 10, wherein the display and the monitoring device are integrated.

17. The non-transient computer readable medium according to claim 10, wherein the electronic device is configured to collect statistical data related to the monitoring.

18. The non-transient computer readable medium according to claim 17, wherein the statistical data includes at least one of the following:
  a) a reading speed statistic;
  b) a reading speed statistic associated with parts of the output;
  c) a reading statistic;
  d) a stimulation statistic; or
  e) a combination of the above.

19. The non-transient computer readable medium according to claim 10, wherein the stimulating is adaptive.

20. The non-transient computer readable medium according to claim 10, wherein the attention threshold is a period of time.

21. The non-transient computer readable medium according to claim 10, wherein the attention threshold is adaptive.

22. The non-transient computer readable medium according to claim 10, wherein the tracking includes the user following the output using at least one of the following:
  a) a finger;
  b) an eye;

c) a stylus;
d) a foot;
e) a voice;
f) a curser key; or
g) a combination of the above.

23. The non-transient computer readable medium according claim 10, wherein the monitoring includes monitoring at least one of the following
   a) brainwaves;
   b) body movement;
   c) finger movement;
   d) a pulse;
   e) blood pressure;
   f) perspiration;
   g) respiration;
   h) eye movement;
   i) a stylus;
   j) a foot;
   k) a voice;
   l) a computer keyboard;
   m) a curser key;
   n) mouse; or
   o) a combination of the above.

* * * * *